United States Patent
Frangi et al.

(10) Patent No.: US 6,425,876 B1
(45) Date of Patent: Jul. 30, 2002

(54) TIGHTENING DEVICE

(75) Inventors: Giampietro Frangi; Gianluigi Frangi, both of Varese (IT)

(73) Assignee: Pavis Varese S.R.L., ITX ( * ) Notice: Subject to any disclaimer, the term of this patent is extended or adjusted under 35 U.S.C. 154(b) by 0 days.

(21) Appl. No.: 09/381,090

(22) PCT Filed: Mar. 17, 1998

(86) PCT No.: PCT/IT98/00055

§ 371 (c)(1),
(2), (4) Date: Sep. 15, 1999

(87) PCT Pub. No.: WO98/41174

PCT Pub. Date: Sep. 24, 1998

(30) Foreign Application Priority Data

Mar. 18, 1997 (IT) .......................................... VA97A0006

(51) Int. Cl.⁷ .............................. A61F 13/00; A61F 5/37
(52) U.S. Cl. .............................. 602/60; 602/62; 602/63; 128/882
(58) Field of Search ............................... 602/5, 20, 23, 602/60–65, 75–77; 606/213–216; 604/393–402; 2/161.2, 161.3, 16, 337, 338, 340, 311, 319, 22, 24; 36/51; 128/DIG. 15, 846, 878, 869, 882

(56) References Cited

U.S. PATENT DOCUMENTS

| | | | | | |
|---|---|---|---|---|---|
| 2,015,255 A | * | 9/1935 | Charpier et al. | ............... | 602/62 |
| 3,000,378 A | * | 9/1961 | Zieman | .................. | 602/62 |
| 3,298,366 A | * | 1/1967 | Moore et al. | ............... | 602/61 |
| 3,680,554 A | * | 8/1972 | Sanchez | ..................... | 128/134 |
| 3,856,008 A | * | 12/1974 | Fowler | ..................... | 602/62 |
| 4,042,977 A | * | 8/1977 | Antonious | ................. | 2/161.5 |
| 4,079,527 A | * | 3/1978 | Antonious | ..................... | 36/51 |
| 4,486,965 A | * | 12/1984 | Friton | .................... | 36/50.1 |
| 5,176,703 A | * | 1/1993 | Peterson | .................. | 602/41 X |
| 5,263,970 A | * | 11/1993 | Preller | ...................... | 602/58 X |
| 6,108,814 A | * | 8/2000 | Tollini | ............................ | 2/22 |

* cited by examiner

Primary Examiner—Denise Pothier
(74) Attorney, Agent, or Firm—Connolly Bove Lodge & Hutz LLP

(57) ABSTRACT

A tightening and elastic tautness adjustment device for a garment or sanitary protection or alike implement to be tightly worn comprises: at least a first elastic textile band formed of a plurality of parallel elastic strips (2) extending from a first edge of said garment or sanitary protection, their free ends being sewn onto a first strip (8) of hooked "Velcro" material, and at least a second elastic textile band similarly formed of a plurality of parallel elastic strips (2') extending from a second edge of said garment or sanitary protection opposed to the first edge, and interlaced with the parallel strips (2) of the first band, their free ends being sewn onto a second strip of hooked "Velcro" material. Said mutually interlaced multistrip elastic bands, being stretchable by pulling apart the two "Velcro" strips, the opposite edges of the sanitary protection or garment pulling toward another and the two "Velcro strips may then be anchored on cooperating "Velcro" pads present on the outer surface of the sanitary protection or garment. The ends of the parallel elastic strips of each band may be permanently sewn onto the respective opposite edges of the sanitary protection or garment, or onto a second pair of "Velcro" strips for realizing the device in a removable form.

4 Claims, 2 Drawing Sheets

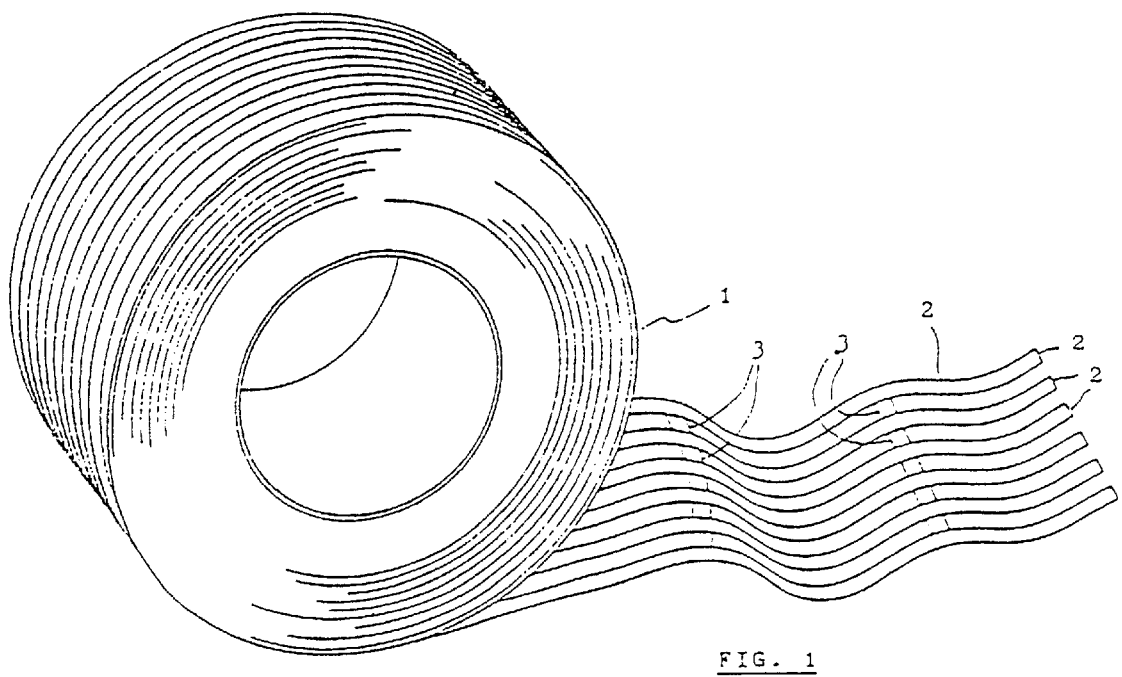
FIG. 1
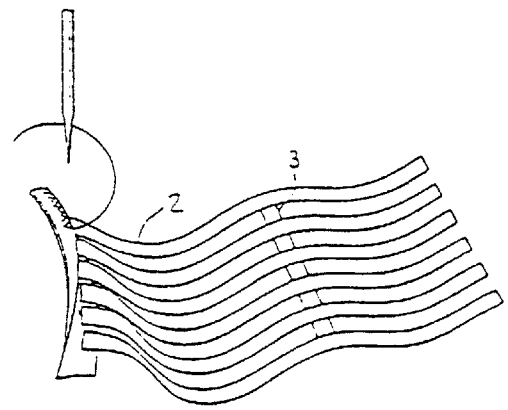
FIG. 2
FIG. 3
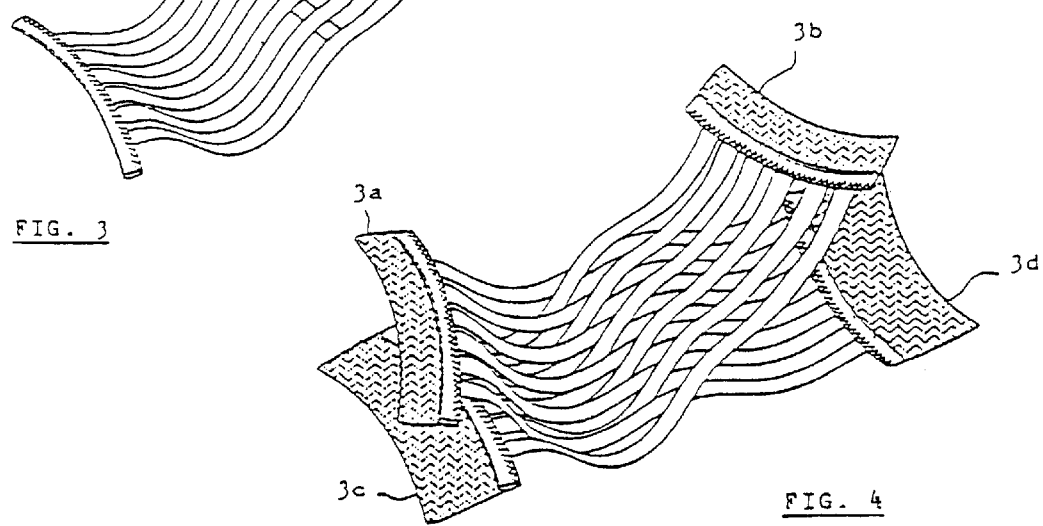
FIG. 4

TIGHTENING DEVICE

The present invention relates to garments and sanitary protections which can be tightly worn on a body part or articulation to be protected or aided in its mechanical action. The invention is particularly useful for makins ankle-bands, leggings, knee-bands, general purpose elastic belts, elastic wrist bandages, special outfits for sport and other highly technical activities, speed outfits, etc.

In making elastic sanitary implements for aiding the mechanical action of articulations, in order to recover their full functionality after injuries or as a form of prevention in performing sporting activities involving relatively high stresses on muscles and/or articulations, it is necessary to ensure, besides the comfort of use, a good adjustability of the elastic tautness.

The conventional tubular elastic sanitary protections are obviously not capable of satisfying the adjustability requirement and can be produced only in a series of relatively standardized sizes.

For uses absolutely requiring the possibility of adjustment, both for the effectiveness of the elastic guard and for comfort, a common lacing must be used for joining two opposite edges of an elastic sanitary band or garment so as to allow to control the tautness and/or to modulate it along its length. The adjustment of the tautness by loosening or tightening the lacing is a wearisome and not very practical operation. In order to obviate the laboriousness of a lacing, use is often made of the so-called VELCRO wherein hook and loop fasteners strip material having a population of tiny hooks fasteners on surface is sewn onto an edge of the sanitary protection, garment or footwear and may be pressed into an anchoring engagement on the surface of a cooperating strip of piled fabric. The range of adjustment of the tautness depends obviously upon the size of the area of piled fabric available for anchoring the hooked part of the "Velcro", that is either sewn over the opposite edge of the elastic implement or on the same edae thereof, in which case the band of VELCRO with the tiny hooks is first passed through a eyelet of the opposite edge of the implement and pulled back to anchor it on the sewn pad of piled. fabric. In case VELCRO fasteners are used for closing and tightening a substantially tubular sanitary protection or garment, the proper positioning of the sanitary protection around the articulation to be protected is made difficult by the need of elastically stretching one edge only of the implement before Joining the two cooperating parts of the VELCRO fastener, often resulting in accidental slippings of the sleeve or bandage, which must be repositioned after fastening it.

Furthermore, a modulation of the tautness along a substantially tubular elastic implement is possible only by increasing the number of independently stretchable strings, or VELCRO fasteners along the closure and this often leads to the formation of creases which may be troublesome and cause problems in case of prolonged wearing of the elastic implement.

When several fastening strings or VELCRO fasteners are used for grading the elastically tautness, such strings must be pulled and fastened one by one in succession, by intervening many times for adjusting their mutual arrangement until an optimal tightening is obtained. The non-elastic nature of the tightening strings or of the textile edges onto which are sewn the cooperating strips of intrinsically non-stretching material of the VELCRO fasteners often impairs the uniformity of elastic and pliable properties of the tubular sanitary protection as a whole.

A solution, to the above noted limitations and drawbacks of known closing and tightening devices for elastic garments and sanitary protections, whether provided with normal lacings or VELCRO fasteners is the object of the present invention.

The closing and tightening device of the invention consists of a first elastic textile band composed of a plurality of parallel elastic strips which extend functionally from a first edge of a garment or sanitary protection and have their free ends sewn onto a first strip of a VELCRO material with a population of tiny hooks on one surface, and of a second elastic textile band similarly composed of a plurality of parallel elastic strips which extend functionally from a second edge of the garment or sanitary protection opposed to said first edge and are interlaced with the parallel strips of the first band. The free ends of the strips of the second band are sewn onto a second strip of a VELCRO material with a population of tiny hooks on one surface. The two hooked VELCRO strips so sewn to the free ends of the elastic strips of the two interlaced multistrip bands may thus be pulled apart as far as to produce the desired elastic tightening of the worn implement and anchored by pressing them over respective pile surfaces on each side of the edges of the closure of the implement, without inducing any undue rotation or slipping thereof. Of course, one strip of VELCRO may be fastened to one edge first and the other strip of VELCRO away as needed, before fastening it to the other edge.

The two multistrip elastic textile bands may constitute themselves a portion or even the only stretchingly elastic portion of a tubular garment or sanitary protection, e.g. when the remaining portion of the garment on the closing edges to which the two multistrip bands are sewn is made of a non-elastic material, for example of leather as it is often the case of leggings and footwear.

Upon stretching and fastening the two VELCRO ends on the outer surface of the sanitary protection or garment, the opposite edges thereof, pulled by the two interlaced textile multistrip bands, may abut on one another or remain spaced apart by a certain distance or gap that is covered by the interlaced parallel elastic strips belonging to the two bands that form the tightening device of the invention.

According to an alternative embodiment of the tightening device according to the invention, the two interlaced multistrip elastic textile bands may have both their ends (i.e. both the ends of each parallel elastic strips forming the band) sewn on two substantially identical strips of hooked VELCRO material, so as to form a removable tightening device that is usable for joining together two opposite edges of a textile sanitary protection or garment provided with VELCRO anchoring pads (pile surfaces) of sufficiently large sizes.

The application of the tightening device may be done by fastening one hooked VELCRO strip of a first band onto a first edge, and one hooked VELCRO end of the other band onto the other edge, then by pulling the two free hooked VELCRO ends of the two interlaced bands for suitably tightenings and stretching the sanitary protection or garment before fastening them on VELCRO anchoring areas at a certain distance from the edge of the closure of the sanitary protection or garment.

A special elastic textile article of manufacture composed of a plurality of parallel strips regularly spaced apart from one another and joined at a regular intervals by transverse textile splicings, greatly simplifying the making of the stretching devices of the invention by facilitating the operations of cutting and sewing the ends of the parallel elastic strips of the two interlaced bands onto strips of VELCRO material and/or onto opposite edges of the closure of the sanitary protection or garment to be elastically tightened.

The series of textile splices extending transversally and joining together the parallel elastic strips represent as many undivided areas for cutting the multistrip band and sewing one end of the multistrip band onto the corresponding edge or on an hooked VELCRO material strip.

The various aspects and advantages of the invention will be even more evident through the following detailed description of some preferred embodiments thereof, and by referring to the attached drawings, wherein:

FIG. 1 shows an elastic textile article of manufacture specially produced for making the tightening devices according to the present invention;

FIGS. 2, 3 and 4 show consecutive steps of preparing a tightening device according to the invention;

Figure 5:
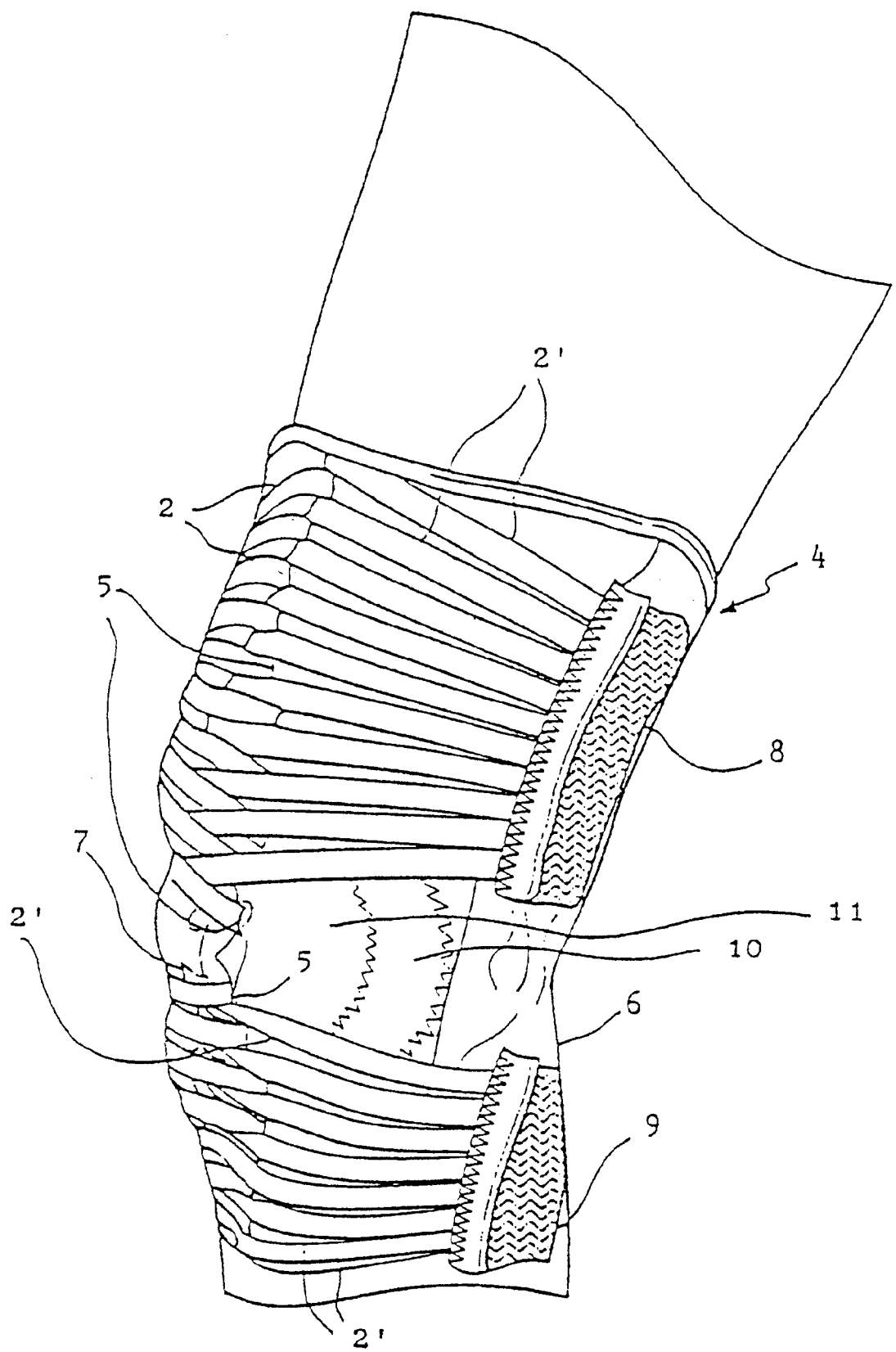
FIG. 5 shows a worn knee-band having a tightening device according to the invention.

Referring to FIG. 1, elastic textile multistrip bands each composed of a plurality of parallel elastic strips, particularly suited for making tightening devices according to the present invention, may be advantageously cut from an elastic textile article of manufacture 1, specially produced for this purpose and having the structure represented in the drawing.

An elastic textile multistrip band may be produced in a continuous form and is constituted by a plurality of parallel elastic textile strips 2, regularly spaced apart from one another, the spacing distance between two adjacent parallel strips being preferably equal to the width of the strips themselves or greater.

At regular intervals, the parallel elastic strips 2 are joined by transversal textile splicings 3, along which the textile band can be cut for obtaining the needed pieces. Furthermore, the uninterrupted transversal textile strip 3 joining parallel elastic strips 2 together provides for a suitable area for sewing the cut edge of the elastic multistrip band along an edge of fabric or along the edge of a strip of hooked VELCRO material 3, as depicted in FIGS. 2, 3 and 4.

According to an embodiment of the device of the invention, as represented in FIG. 4, two elastic multistrip textile bands, once their parallel elastic strips have been interlaced, have the ends of their parallel elastic strips sewn onto the four strips of hooked VELCRO material: 3a, 3b, 3c and 3d.

The article of FIG. 4 is a multipurpose removable tightening device that can be applied to two opposite edges of a sanitary protection or garment, provided with a suitable areas or pads with a surface morphology (pile) suitable for anchoring the strips of hooked VELCRO material.

The working of the device is quite evident.

A pair of VELCRO strips (strips 3c and 3d of the sample shown in FIG. 4) are first fastened along the opposite edges of a sanitary protection or garment. Then, the other two VELCRO strips 3a and 3b are pulled apart and anchored in a desired position over VELCRO anchoring pile pads on the implement, in proximity to the strips of VELCRO material belonging to the other band of the pair of interlaced multistrip bands.

Alternatively, one end of each of the parallel elastic strips of each interlaced band may be permanently fastened, e.g. by sewing, to a corresponding edge of the sanitary protection or garment and only the other ends of each of the parallel elastic strips of each bands is sewn onto strips of hooked VELCRO material. These two strips will be the only ones to be anchored in position on pads of suitable fabric (pile) present on the outer surface of the sanitary protection or garment, at a certain distance from each edge of the sanitary protection or garment.

This second embodiment of the invention, that may be preferable in many applications, is depicted in FIG. 5, in the form of a knee-band worn around the articulation and indicated with 4 as a whole.

In the shown sample, the ends of the parallel elastic strips 2 of the two distinct pair of interlaced multistrip bands are permanently sewn along edge 5 of an elastic textile article that may be wound to form a tubular sleeve 6 that can be loosened. Likewise, the ends of parallel elastic strips 2' of a second distinct pair of interlaced multistrip bands, which are interwoven with the elastic strips 2 of the first pair of multistrip bands, are permanently fastened along the opposite edge 7 of the split sleeve 6.

After having interlaced the strips 2 and 2' of the two multistrip bands, the free ends of the strips of each band of the pair are sewn onto corresponding strips of hooked "VELCRO" material, 8 and 9 (VELCRO strips connected to strips 2' on the opposite side sleeve 6 are not visible).

The semicircular portions 10 and 11 may be textile paddings or define a "pocket" for housing a resilient ring or pad, e.g. made of latex, for proctecting the rotula, etc.

The knee-band may easily be worn by slipping it from the foot while in an open condition, i.e. when the free ends of the two pairs of interlaced multistrip bands are left loose, thus fully exploiting the capacity of extension of the sleeve through the full length of the strips of the two pairs of interlaced bands and even beyond, thanks to the elasticity of the bands.

After having properly disposed the implement in a position whereby the portions 10 and 11 or the corresponding latex pads fit over top of patella, the two free ends of a first pair of interlaced elastic bands, e.g. the free ends of the lower pair of band 2 and 2', are stretched apart as far as tightening as desired the lower part of the knee-band and the two "VELCOR" end strips are anchored in position on cooperating VELCRO anchoring pads present on the outer surface of the textile sleeve 6.

Subsequently the free ends of the upper pair of interlaced elastic band 2 and 2' are pulled apart, also in this case exerting the desired stretching action before fastening the two VELCRO ends on the corresponding anchoring pads on the outer surface of the knee-band.

Obviously, it is not necessary to use two distinct pairs of interlaced bands, i.e. to divide the tightening device into a lower part and an upper part, however by such a division an easier and more accurate adjustment of the elastic tautness is favored. Indeed, it is made possible to differentiate the tautness above and below the articulation. This possibility of modulating the stretching along the length of a sanitary protection or garment remains available even if the tightening device is initially produced by using a single pair of undivided multistrip bands, i.e. only two VELCRO strips. Even in these cases it is always possible to "personalize" the tightening device by dividing it into two or more distinct pairs of independently stretchable interlaced elastic bands, simply by transversally cutting the strip of VELCRO material onto which the free ends of the parallel elastic strips of each band are sewn. Thus, a tightening and stretching device may be divided into two or more, independently stretchable, "pairs" of interlaced elastic bands, simply by cutting the VELCRO strip at the free end of the two bands.

An article made according to the invention may be put on the market with an undivided single pair of mutually interlaced multistrip elastic textile bands, leaving to the user the liberty of adjusting its configuration by cutting the two VELCRO strips at the most appropriate point(s).

What is claimed is:

1. An elastic adjustment tautness device comprising:
   (a) a garment having opposing edges;
   (b) at least a first plurality of parallel elastic strips having first and second ends;
   (c) at least a second plurality of parallel elastic strips interlaced with the at least first plurality of parallel elastic strips and having third and fourth ends; and
   (d) said first and second ends of the first plurality of parallel elastic strips including first and second fastening means respectively and said third and fourth ends of the second plurality of parallel elastic strips including third and fourth fastening means respectively,
   wherein said first fastening means of the first plurality of elastic strips and said fourth fastening means of the second plurality of elastic strips are removably attached to opposing edges of the garment and said second fastening means of the first plurality of elastic strips and said third fastening means of the second plurality of elastic strips are removably attached to opposing edges of the garment whereby the first and fourth fastening means provide an anchor when second and third fastening means are pulled to opposing edges of the garment to produce a desired tension.

2. A textile tubular elastic bandage to be tightly and conformally worn around a body articulation having an outer surface and opposing edges to be pulled toward each other and blocked in a position that produces a desired tautness of the tubular bandage, which comprises:
   (a) at least a first plurality of parallel elastic strips secured to and extending from one of said opposing edges and connected at outer ends to a first hook fastener strip;
   (b) at least a second plurality of parallel elastic strips secured to and extending from the other one of said opposing edges, interlaced with the parallel elastic strips of said first plurality and connected at outer ends to a second hook fastener strip;
   (c) at least a first loop anchorage pad on an area of the outer surface of said textile tubular bandage close to said other one of said opposing edges;
   (d) at least a second loop anchorage pad on an area of the outer surface of said textile tubular bandage close to said first one of said opposing edges;
   whereby said first hook fastener strip and said second hook fastener strip are pullable apart in opposite directions and slantable in respect to each other to produce a desired tension of each parallel elastic strip of said first and second plurality of interlaced parallel elastic strips and anchored on said first and second loop anchorage pads, respectively.

3. The textile tubular bandage of claim 2, comprising at least two pairs of said interlaced first and second plurality of parallel elastic strips, independently stretchable and anchorable with respect to one another.

4. The textile tubular bandage of claim 2, wherein said first plurality of parallel elastic strips and said second plurality of parallel elastic strips extending from the opposing edges include third and fourth hook fastener strips, respectively, and third and fourth loop anchorage pads on the outer surface of the bandage for removably securing the third and fourth hook fastener strips thereon.

* * * * *